(12) United States Patent
Penny et al.

(10) Patent No.: US 6,409,724 B1
(45) Date of Patent: Jun. 25, 2002

(54) ELECTROSURGICAL INSTRUMENT

(75) Inventors: Keith Penny, Monmouth; Francis E Amoah, Cardiff; Colin Charles Owen Goble, South Glamorgan, all of (GB)

(73) Assignee: Gyrus Medical Limited, Cardiff (GB)

( * ) Notice: Subject to any disclaimer, the term of this patent is extended or adjusted under 35 U.S.C. 154(b) by 0 days.

(21) Appl. No.: 09/576,630

(22) Filed: May 24, 2000

Related U.S. Application Data

(60) Provisional application No. 60/141,262, filed on Jun. 30, 1999.

(30) Foreign Application Priority Data

May 28, 1999 (GB) .............................................. 9912627

(51) Int. Cl.[7] .............................................. A61B 18/18
(52) U.S. Cl. .............................. 606/41; 606/45; 606/51
(58) Field of Search .............................. 606/41, 42, 45, 606/48, 49, 50, 51, 170

(56) References Cited

U.S. PATENT DOCUMENTS

| | | | |
|---|---|---|---|
| 3,999,552 A | 12/1976 | Huggins | |
| 4,116,198 A | 9/1978 | Roos | |
| 4,641,649 A | 2/1987 | Walinsky et al. | |
| 5,217,459 A | 6/1993 | Kamerling | |
| 5,300,068 A | * 4/1994 | Rosar et al. | 606/32 |
| 5,370,644 A | 12/1994 | Langberg | |
| 5,405,346 A | 4/1995 | Grundy et al. | |
| 6,004,320 A | * 12/1999 | Casscells et al. | 606/170 |
| 6,016,452 A | * 1/2000 | Kasevich | 606/41 |
| 6,193,715 B1 | * 2/2001 | Wrublewski et al. | 604/22 |

FOREIGN PATENT DOCUMENTS

| | | |
|---|---|---|
| EP | 0 865 768 A | 9/1998 |
| WO | WO 94/26188 A1 | 11/1994 |
| WO | WO 90/06079 | 6/1999 |

* cited by examiner

*Primary Examiner*—Roy D. Gibson
(74) *Attorney, Agent, or Firm*—Oliff & Berridge, PLC

(57) ABSTRACT

An electrosurgical instrument has coaxial inner and outer tubular members (1,2) made of a conductive material to form a coaxial transmitting line. The inner member (1) is preferably dimensioned to receive a laparoscopic tool with the working elements of the tool projecting beyond a distal end (1D) of the inner member (1). Alternatively, the inner member (1) may, itself, incorporate a working element at its distal end. The outer member (2) is connected to the inner member (1) at a distance from the distal end (1D) of the later, and a radio frequency (r.f.) feed (4) is connected to the inner member (1) distally of the connection (7) between the inner and outer members. Between the connections there is an r.f. isolating structure formed by or associated with the inner member (1) to present a series impedance between the connections (4,7) at an operating frequency of the instrument.

28 Claims, 5 Drawing Sheets

ELECTROSURGICAL INSTRUMENT

This nonprovisional claims the benefit of U.S. Provisional Application No. 60/141,262, filed Jun. 30, 1999.

FIELD OF THE INVENTION

This invention relates to an electrosurgical instrument and, in particular, to apparatus for converting a surgical instrument, such as a purely mechanical laparoscopic tool, for electrosurgical treatment

BACKGROUND OF THE INVENTION

In the field of laparoscopic surgical tools, the ability to deliver radio frequency electrosurgical power for coagulation is well known. It is also well known for laparoscopic tools to provide for mechanical manipulation or a mechanical function. Tools combining these attributes include metal instruments with insulated shafts that can be used as monopolar instruments. There are several problems with such tools. Firstly, monopolar power delivery can cause excessive tissue damage as a result of the long conductive pathways. This is particularly so when attempting to deep perform deep coagulation which involves high curt delivery. A second problem is that such high current delivery stresses the electrical interface between tissue and electrodes, causing carbonisation and/or sticking. Yet another problem is that a metal instrument shaft can cause radio frequency energy to be capacitively coupled to entry ports or other closely coupled instruments.

One technique used in the prior art to overcome these problems is to use a bipolar instrument. In this case two electrodes are used to deliver electrical power to tissue. This localises the power distribution and lessens the danger of damage to adjacent structures. However, such instruments are more complicated particularly when movable elements are required such as for forceps or scissors. Further, the depth of effect is determined by the spacing of the electrodes from each other.

It is an object of the present invention to provide an improved instrument.

SUMMARY OF THE INVENTION

According to a first aspect of this invention, an electrosurgical instrument comprise: an elongate inner tubular member having a proximal end and a distal end, at least a portion of the member being electrically conductive in order that there is d.c. electrical continuity between the said ends; and an elongate tubular electrically conductive sheath surrounding the inner member but spaced from the conductive material of the inner member to form an electrically insulative jacket, whereby the member and the sheath constitute a coaxial transmission line, the sheath being electrically connected to the inner member at a location spaced proximally from the distal end; a feeder connected to the inner member distally of the connection between the sheath and the inner member, and an r.f. isolating structure between the said connections of the inner member to the feeder and to the sheath, the isolating structure presenting a series impedance between the said connections at an operating frequency of the instrument The form of the isolating structure depends on the frequency of operation. In general, it is constituted by a resonant element or a resonant assembly of elements having a frequency of resonance corresponding to an operating frequency of the instrument. For comparatively high electrosurgical frequencies, typically upwards of 300 MHz, the isolating structure consists of a section of the inner member between the connections to the sheath and the feeder, the section having an electrical length of $m\lambda/4$, where m is an odd number and $\lambda$ is the wavelength associated with the operating frequency in question. Since, at the proximal end of this section, the sheath is coupled to the inner member at least at high frequencies, the section operates as an impedance transformer presenting a high impedance at the connection with the feeder. At lower frequencies, humped components are preferred, such as an inductance formed by a section of the inner member between the connections to the sheath and feeder, this inner member section being surrounded by a body of high permeability material such as a ferrite ring. A resonating capacitor is coupled between a ground connection which may be the sheath, and a conductor of the feeder which is connected to the inner member, so as to produce a parallel resonant structure at the operating frequency.

It is possible to construct an isolating structure which isolates the proximal end of the inner member from the feeder connection at two widely spaced operating frequencies, for instance, at an upper operating frequency above 300 MHz and a lower operating frequency below 300 MHz. Typical frequencies are 2.45 GHz and 5 MHz respectively. In this case, two sections of the inner member which are electrically in series with each other constitute elements of respective resonant assemblies or unit at the upper and lower frequency respectively. The first section may extend between the connection of the inner member to the feeder and a decoupling capacitance between the inner member and the sheath, while the second section extends between the decoupling capacitance and a d.c. connection of the sheath to the inner member, this latter connection being the further from the distal end of the inner member. The first section has the quarterwave electrical length feature described above, while the second section is surrounded by high permeability material so that the two sections respectively provide the impedance transformer and series inductance for isolation at the upper and lower frequencies. It will be understood that the decoupling capacitance resents a low impedance connection between the sheath and the inner member at the upper frequency, but not at the lower frequency. At the lower frequency, the first section appears as a low series impedance.

The insulating jacket between the conductive material of the inner member and that of the sheath may perform a dual function, insofar as not only does it provide a dielectric medium of a coaxial transmission line comprising the inner member as an inner conductor and the sheath as an outer shield, but also it may serve as an optical path for illumination of the operation site adjacent the distal end of the inner member or for viewing of the site, the instrument acting as an endoscope. Thus, the space between the inner member and the sheath may be occupied by dielectric optical material such as glass or transparent plastics, formed as a tube, a rod, or as fibres. This optical material may also serve as a support for tile inner member within the sheath.

According to a second aspect of the invention, there is provided an electrosurgical instrument for electrosurgical treatment at an operating frequency of at least 300 MHz, comprising an elongate electrically conductive lumen housing a mechanically or optically functional element, an electrode at a distal end of the lumen and electrically coupled to the lumen, an elongate electrically conductive outer sheath coaxially arranged around the lumen and having a distal end adjacent the lumen distal end, the sheath being dimensioned to enclose an insulative layer (which may be air) such that the sheath and the lumen together form a coaxial transmission line, and an isolating structure associated with the distal end of the sheath to restrict the flow of electrosurgical current in the sheath According to a second aspect of the invention, there is provided an electrosurgical tool converter for converting an elongate surgical tool into an electrosurgical instrument for performing electrosurgical treatment at an operating frequency of at least 300 MHz, the converter comprising an elongate electrically conductive lumen for receiving the tool with a working element of the tool exposed beyond an open distal end of the lumen to form an electrode electrically coupled to the lumen, an elongate electrically conductive outer sheath coaxially arranged around the lumen and having a distal end adjacent the lumen distal end, the sheath being dimensioned to enclose an native layer such that the sheath and the lumen together form coaxial transmission lint, and an isolating structure associated with the distal end of the sheath to restrict the flow of electrosurgical currents in the sheath.

The isolating structure may comprise a balun, typically a quarter-wave sleeve balun, arranged to yield a substantially balanced feed location in the region of the distal end of the sheath where, generally, a working element of the instrument is attache, e.g. a pair of forceps jaws or scissor jaws.

In preferred embodiments of the invention, the is proximally coupled to the lumen in respect of electrical currents at the operating frequency, and the lumen itself is coupled to a fed structure at a location spaced axially from the coupling to the sheath. The axial spacing is such that, at the operating frequency, the lumen may be electrically short-circuited to the sheath, the sheath and the lumen being isolated from ten feed structure at that point at the operating frequency. Typically, the distance between the sheath-to-lumen coupling and the coupling of the feed structure to the lumen is a quarter-wavelength, the wavelength being the electrical wavelength of electrosurgical energy in the transmission line formed by the sheath and the lumen The axial distance between the feed structure and each discontinuity in the sheath, particularly the distal end of the sheath, is preferably such that the corresponding electrical length is one half wavelength or a multiple thereof in order that the transmission line formed by the sheath and the lumen need not have the same characteristic impedance as that of the feed structure. A multiples λ/2 structure yields a source impedance at the end remote from the feed structure corresponding substantially to the characteristic impedance of the feed structure. Indeed, it is possible to construct the transmission line so as to have more than one section of different characteristic impedances due, for instance to the sheath having portions of differing diameters. In such circumstances, each section preferably has an electrical length which is an integer multiple of λ/2.

Delivering electrosurgical power at frequencies between 300 MHz and 100 GHz provides several advantages. The electrosurgical energy is propagated predominantly by dielectric means, which means that the conductive electrode/tissue interface is less important that at lower frequencies. By confining the electric field it is possible to define the treatment area in such a way that comparatively large areas may be treated with small electrodes. For cost benefit, particularly with regard to manipulable instruments such as forceps, the working elements can be constructed of a dielectric material with an embedded conductor rather than by more expensive metal fabrication techniques. UHF energy absorption, particularly at the ISM (Industrial/Scientific/Medical) frequency of 2450 MHz, is determined by water content, which means that variable tissue performance is virtually eliminated. For example, in conventional low frequency electrosurgery, performance is determined by conduction. Fat can have a conductivity which is a mere fraction of highly conductive body fluids such as blood or bile. The water content values, however, are not very different and UHF performance is consequently not as variable.

The proximal trap and the distal balun referred to above allow electrosurgical currents to be isolated to selected areas of the instrument at UHF operating frequencies. Thus, even though the instrument may have electrical continuity throughout its construction due, for instance, to the lumen and the sheath being conductive throughout their length, only selected areas carry electrosurgical currents and voltages. For instance, the instrument, or a combination of the instrument and an inserted non-electrosurgical tool may have an exposed metal handpiece or handle with electrical continuity to the treatment area without danger to the user. This also means that the tool may be made entirely of metal, including a rod actuator and the like within the lumen, and may, therefore, be made more robust.

The sheath is typically fed from a proximally located lateral aperture by a coaxial transmission line or, at frequencies above 5 GHz, a waveguide. The annular cross-section space between the lumen and the sheath may contain a dielectric medium, which may include fibre optics or rod lenses for illumination and visualisation, and fluid passageways for fluid delivery or extraction.

The selective coupling of UHF electrosurgical energy, as described above, allows conversion of standard laparoscopic instruments or endoscopes, for electrosurgical use on tissue The invention is also applicable to laparoscopic electrosurgical instruments. Thus, there may be provided, in accordance with the invention, an electrosurgical instrument comprising the combination of a tool converter as mentioned above and a surgical tool housed in the lumen, the tool having a working element projecting beyond the distal end of the lumen to form an electrode for electrosurgical treatment of tissue, and a handpiece projecting beyond a proximal end of the lumen.

The instrument may be adapted to operate additionally at comparatively low frequencies, i.e below 300 MHz and typically between 100 kHz and 40 MHz. In this case a choke may be placed around the lumen at a proximal end of the transmission line formed by the sheath and the lumen, to prevent conduction of low frequency electrosurgical currents proximally along the lumen or the shaft of a surgical tool housed in the lumen. The same feed structure may be used for delivering both low frequency and UHF electrosurgical energy. The choke forms a lumped impedance circuit, and the return path back to the r.f. source connected to the feed from the tissue is by way of stray capacitance between the patient and the return conductor, which may be referenced to ground potential.

The invention will be described below by way of example with reference to the drawings.

BRIEF DESCRIPTION OF THE DRAWINGS

In the drawings:

Referring to FIG. 1, apparatus for convening a laparoscopic surgical tool into an electrosurgical instrument comprises an internal lumen 1 in the form of an elongate conductive tube, and an elongate electrically conductive outer sheath 2 coaxially arranged around the lumen 1 and having a distal end 2D) adjacent the lumen distal end 1D. The sheath 2 is dimensioned to enclose an insulative layer 3 such that the sheath and the lumen together form a coaxial transmission line extending from a feed structure 4 to the distal end 2D of the sheath 2 where the lumen 1 has a projecting distal end portion terminating in distal end 1D. The distal end portion of the sheath 2 is configured as an isolating structure in that, in this embodiment, the sheath has an inner distal end portion of reduced diameter formed as a tube 5 within the main tubular body 6 of the sheath. The tube 5 is electrically connected at its proximal periphery to the main body 6 at a position such that the main body 6 and the inner portion 5 are in an overlapping configuration with a thin annular space between them. This space may be occupied by a material (not shown) having a different dielectric constant than that of the medium within the manual sheath interior 3. The electrical length of the overlapping portion is arranged to be a quarter-wavelength, or a odd multiple quarter-wavelength so that the main body 6 of the sheath 2, where it overlaps the inner portion 5, forms a sleeve balun promoting a generally balanced condition when the lumen 1 emerges from the sheath at its distal end 2D. This structure, in conjunction with a low impedance connection 7 (in this case an electrical short circuit) between the sheath at is proximal end 2P and the lumen 1, allows an electrosurgical field to be developed at the distal ends of the lumen and the sheath whilst maintaining substantially ground potential along the length of the sheath proximally of the balun.

Figure 1B:
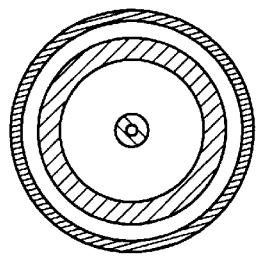
FIGS. 1A and 1B are longitudinal and transverse cross-sections of a first tool converter with accordance with the invention, for operation at 2450 MHz.

It will be noted that the r.f. feed structure 4 comprises a coaxial feeder with an inner conductor 4I passing through a lateral aperture 8 in the sheath 2 to a connection with the lumen 1 at a point spaced from the low impedance connection 7. This spacing ("B") is an odd multiple of the quarter-wavelength m$\lambda$/4 (m is preferably equal to 1), allowing the isolation of the lumen 1 distally of the feed structure 4 from ground, given that the lumen is grounded at its proximal end by virtue of its connection to the sheath 2 which is connected to the screen of the r.f. feed 4.

Figure 6:
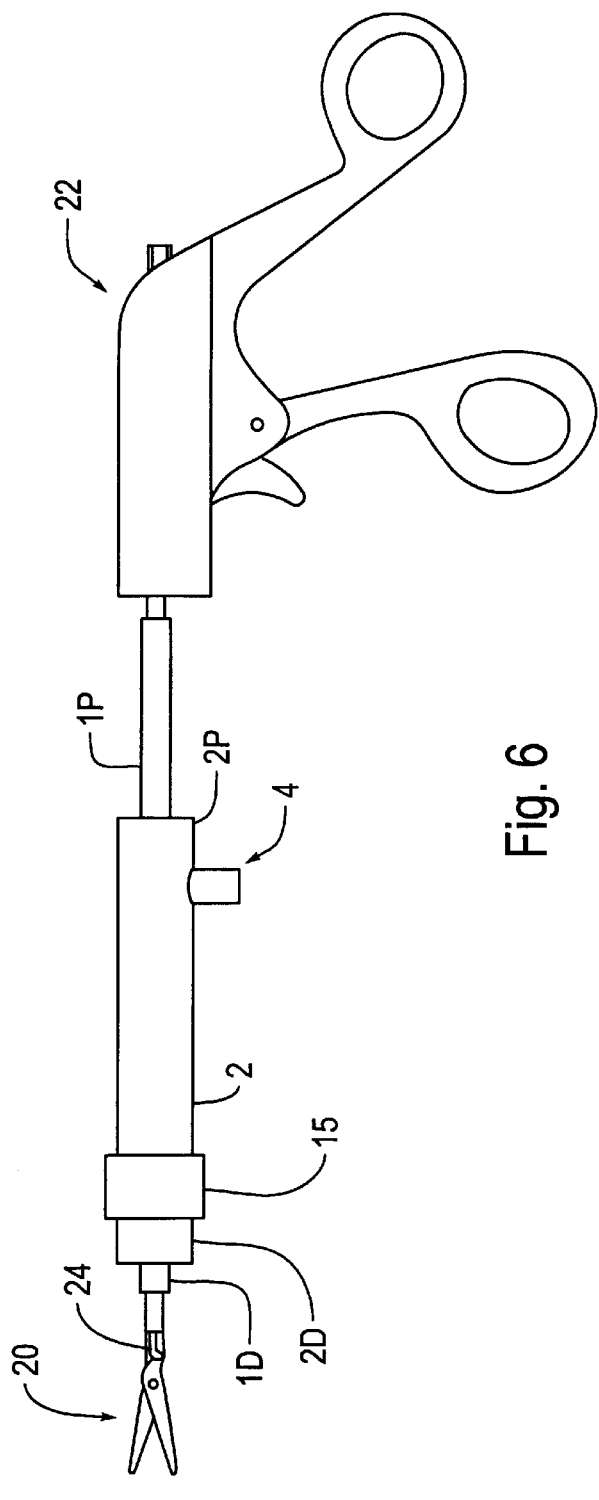
FIG. 6 is a diagrammatic side view of electrosurgical scissors incorporating the tool converter of FIGS. 2A and 2B.
Figure 7:
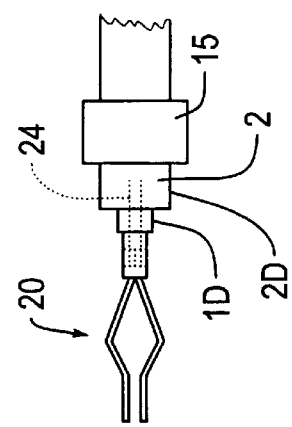
FIG. 7 is a diagrammatic side view of part of an electrosurgical forceps instrument incorporating the tool converter of FIGS. 2A and 2B.

Typically, the characteristic impedance of the feed structure or feeder 4 is 50 ohms. The transmission line formed by lumen 1 and sheath 2 (including the inner distal end portion 5), has two sections of two different characteristic impedances. The first of these sections, extending from the feeder 4 to the proximal rim of the inner portion 5, has a first characteristic impedance, typically 10 ohms or less, whilst the second section, represented by the inner distal end portion 5 of the sheath, has a second characteristic impedance somewhat lower that that of the first portion. Since these characteristic impedances are different from that of the feeder and different from each other, the electrical lengths of the inner portion 5 and the complete sheath 2 from the r.f. feed point to the distal end 2D of the sheath 2 are multiples of $\lambda$/2 (the word "multiple" here being indicative of any integer from 1 upwards). This yields, at least approximately, an operating impedance at the distal end equal to the impedance of the feeder 4. The interior passage 1P of the lumen is dimensioned to receive a laparoscopic tool such as a pair of forceps, scissors, or, indeed, an endoscope. Other possibilities will be apparent to those skilled in the art. The tool is fitted in a manner not shown wherein the working elements or working section project from the distal end 1D of the lumen 1 and are electrically coupled to the lumen 1 so as to form an active electrode for electrosurgical treatment of tissue. Embodiments of the invention including scissors and forceps are illustrated in FIGS. 6 and 7, respectively. In each case, the tool has projecting working elements 20 which form an electrode and a handpiece 22. Each has a reciprocable actuation rod 24 connected to the working elements. Neither figure is drawn to scale.

Electosurgcal power coupling at UHF or above may be indirect, by means of capacitive or inductive coupling between the lumen 1 and the in tool.

Typically, such surgical tools are constructed of stainless steel, which is a relatively poor electrical conductor. The lumen 1 is plated with silver or copper on its outer surface. Alternatively, in a case where the lumen 1 forms the shaft of a surgical tool itself, that shaft may have a silver or copper-plated outer layer.

The sheath 2 may be separated from the lumen 1 by low loss dielectric spacers (not shown), or the space 3 may be occupied by dielectric optical fibres or rods which, as well as performing an optical function for illumination and/or visualisation of the operative site, serve to support the lumen within the sheath.

Figure 1A:
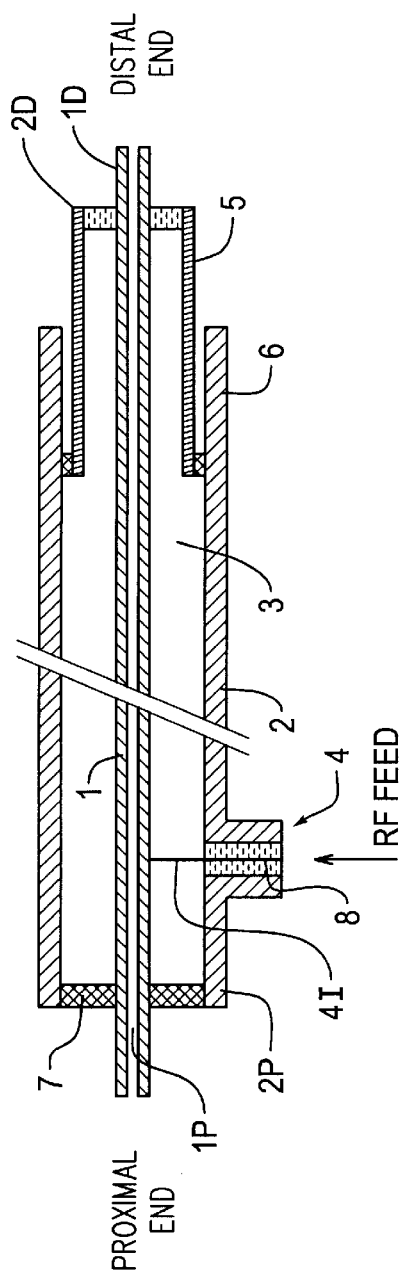

The diameter of the sheath is largely governed by the required characteristic impedance. It should be borne in mind that FIG. 1 is diagrammatic and is not intended to be a scale drawing. For a characteristic impedance of 50 ohms or upwards, the ratio between the inner diameter E of the sheath and the outer diameter F of the lumen is quite high, to the extent that the structure shown in FIG. 1 could have a diameter typically three times that of the surgical tool inserted in it. In the case of the space 3 between the lumen 1 and the sheath 2 being used for optical fibres or a fluid conduit, this high ratio may be advantageous. However, coagulation performance is often improved by use of a lower characteristic impedance, the target issue having an impedance typically lower than 50 ohms. In these circumstances, the ratio of the sheath inner diameter to the lumen outer diameter (i.e. E/F) can be reduced Indeed, the sheath may have a characteristic impedance as low as 10 ohms, resulting in an instrument diameter in the order of only 20% to 30% greater than at of the inner diameter of the lumen 1 (typically accepting a 4-French or 5-French tool).

Preferably, a quarter-wave transformer section (not shown) comprising a transmission line of intermediate characteristic impedance is inserted in series between the 50 ohm feeder 4 and the aperture 8 to match the characteristic impedance of the combination of the sheath 2 and the lumen 1 to that of the feeder 4. This transformer may be part of the feeder itself integrated in the tool converter structure which includes the sheath 2. This avoids the standing waves produced when there is an impedance mismatch, even though the effects of these can be ameliorated by using half-wavelength structures as described above. As is well known in the art, the impedance of such a transformer (which is not shown in the drawings), is the geometric mean of the two impedance being matched.

Figure 2B:
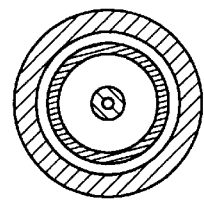
FIGS. 2A and 2B are similar cross-sections of a modified version of the tool converter of FIG. 1.
Figure 2A:
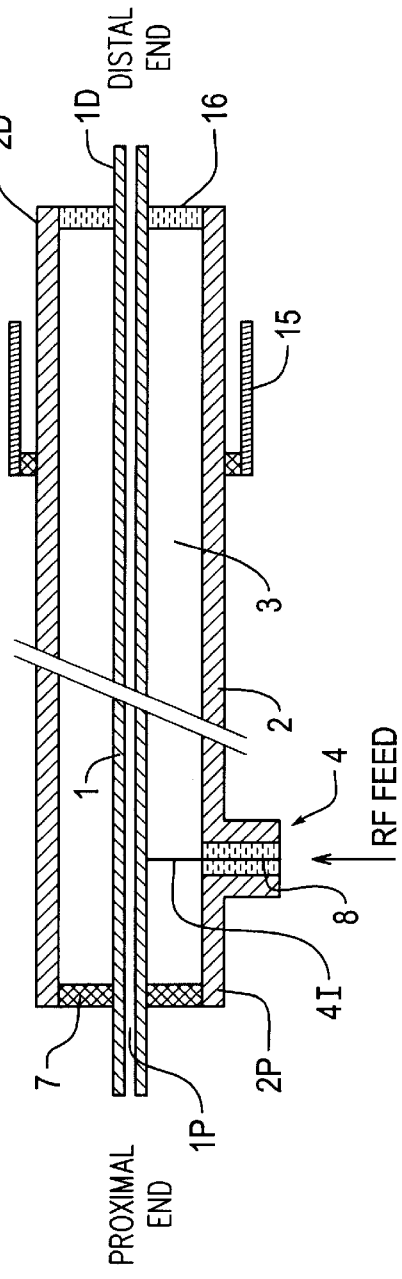

A modified version of the apparatus of FIG. 1 is illustrated in FIG. 2. Referring to FIG. 2, the quarter-wave balun is formed differently from that of FIG. 1 inasmuch as the sheath 2 has a constant internal diameter between the feeder 4 and the sheath distal end 2D. Instead of providing an inner distal end section as in the FIG. 1 embodiment, the sheath 2 is provided with a quarter-wave sleeve 15 having one rim electrically connected the main body of the sheath 2, its other rim being open circuit, with the electrical length of the thin annular space between the two components being equal to λ/4 in the axial direction. Again the sheath projects distally some distance beyond the balun section, and the lumen 1 projects distally beyond the distal end of the sheath 2D, where is it supported by an insulative annulus 16.

Figure 3B:
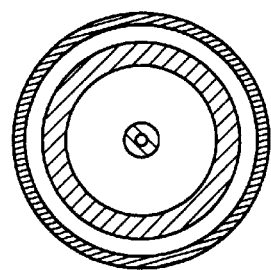
FIGS. 3A and 3B are similar cross-sections of a tool converter having a waveguide feed structure.
Figure 3A:
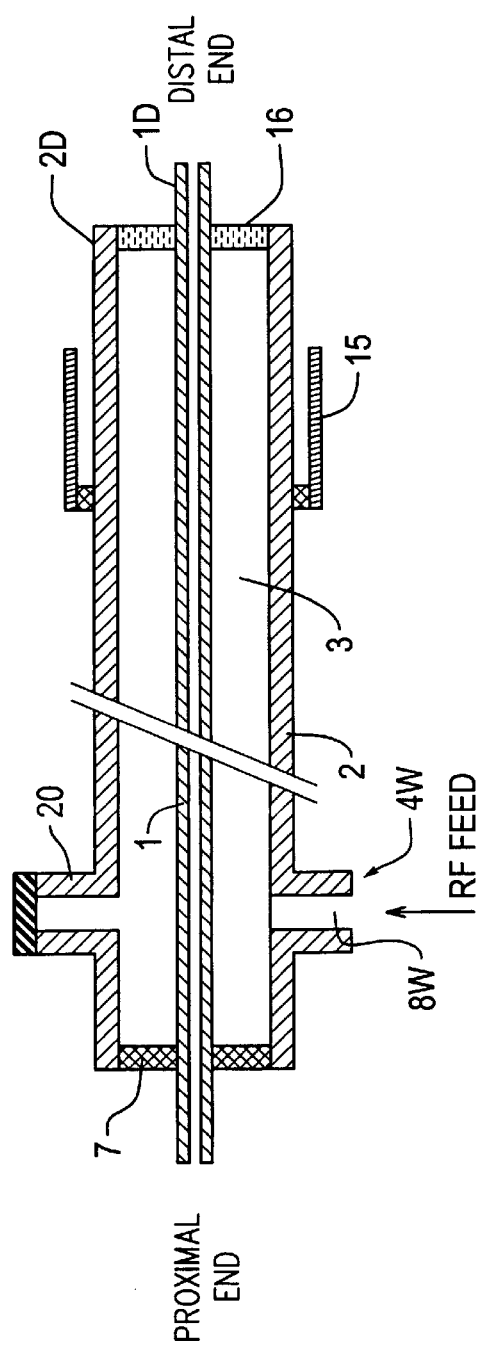

Again, in this embodiment, the preferred total electrical length of the sheath 2 between the feed 4 and the distal end 2D is a multiple of the half-wavelength Referring to FIG. 3, an alternative embodiment for use at frequencies typically above 5 GHz has a waveguide feeder 4W. The cross-sectional dimensions of the waveguide are inversely proportional to the operating frequency, and the waveguide may be filled with a low-loss dielectric material having a dielectric material having a dielectric constant greater than that of air in order to reduce the dimension further. Energy from the waveguide feeder 4W is coupled into to the coaxial transmisssion line is coupled through the lateral aperture 8W in the sheath 2, and thereby coupled to the transmission line formed by the combination of the lumen 1 and the sheath 2. A tubular lateral stub 20 with a short circuited end provides a match between the two transmission line types.

Figure 4B:
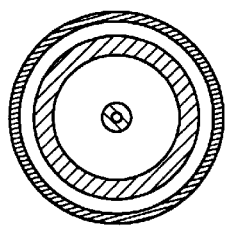
FIGS. 4A and 4B are cross-sections of a tool converter similar to that shown in FIGS. 2A and 2B, but having the ability to operate additionally at frequencies in the region of 100 kHz to 40 MHz.
Figure 4A:
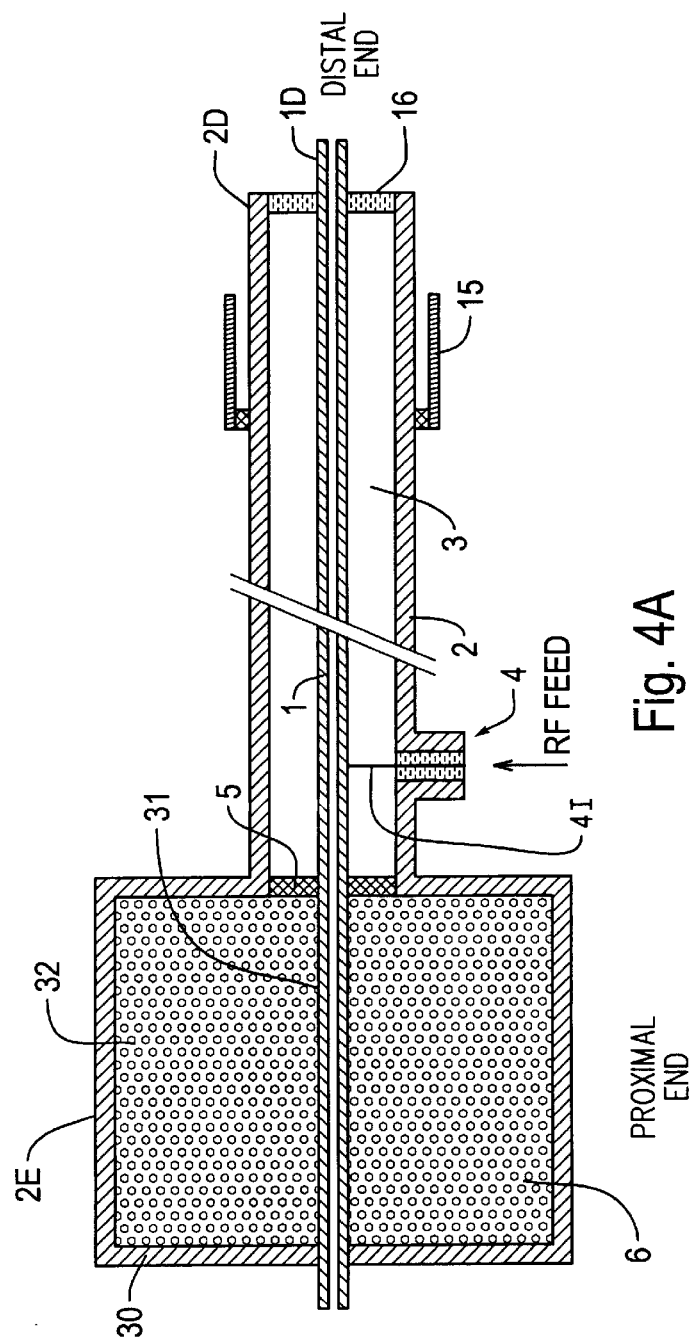

In some circumstances, it can be advantageous to be able to supply electrosurgical energy to a treatment electrode at both UHF or upwards and at a lower frequency using the same instrument. Indeed, it may be advantageous to supply both frequency components simultaneously. This possibility is allowed for in the embodiment of FIG. 4, which is of similar construction to that described above with reference to FIG. 2, but with the additional feature of a high impedance series element between, on the one hand, the connection of the feeder 4 to the central lumen 1 and, on the other hand, the lumen at the proximal end of the sheath 2. In order to achieve operation at lower frequencies (typically 100 kHz to 40 MHz), but also at frequencies generally below 300 MHz a conductive path is provided between the inner surface of the lumen 1 and the inserted instrument shaft (not shown). Electrosurgical energy at UHF is isolated from the proximal end of the sheath and the instrument, as in the embodiments described above with reference to FIGS. 1 to 3, by interconnecting the lumen 1 and the sheath 2 with a low impedance element at an electrically appropriate distance from the feeder 4. In the present embodiment, where a low frequency voltage needs to be developed between the lumen 1 and the sheath 2, the low impedance element is formed as a shunt capacitor 25 which is virtually a short circuit at UHF. Typically the capacitor may comprise a dielectric annulus around the lumen 1, so that the opposed loath 2 and the lumen 1 in this region form a capacitor of sufficiently high value. The low frequency component is independently isolated from the proximal end of the sheath and the instrument by a metallic short circuit in the form of a conductive end plate 30 between the lumen 1 and an enlarged portion 2E of the outer sheath 2, and a series inductance formed by (a) the section 31 of the lumen 1 between the capacitor 25 and the end plate connection 30 and (b) a ring 32 filling the space between the sheath wall of the enlarged portion 2E and the inner lumen 1. The ring 32 is made of a magnetisable material having high permeability, such as a nickel-zinc-ferrite mixture. By way of example, a suitable material for operation at 5 MHz is FairRite nickel-zinc-ferrite mix #61, which has a relative permeability of 120, and a Q in excess of 100 at 5 MHz. The resulting series impedance is the product of the angular frequency, the relative permeability of the ferrite slug 32 and the effective area of the magnetic flux part of the cross-section divided by the effective magnetic flux path length. In this case, a slug of length 30 mm (dimension G), outer diameter 28 mm, and a lumen outer diameter (E) of 2.3 mm, yields an inductive reactance of 40 ohms between the active and ground conductor of the feed 4 at 5 MHz. In order that the inductance 31, 32 forms a resonant circuit at the lower opera frequency, a capacitance is connected between the sheath 2 and the conductor 4I of the feeder 4 connected to the lumen 1.

Figure 5:
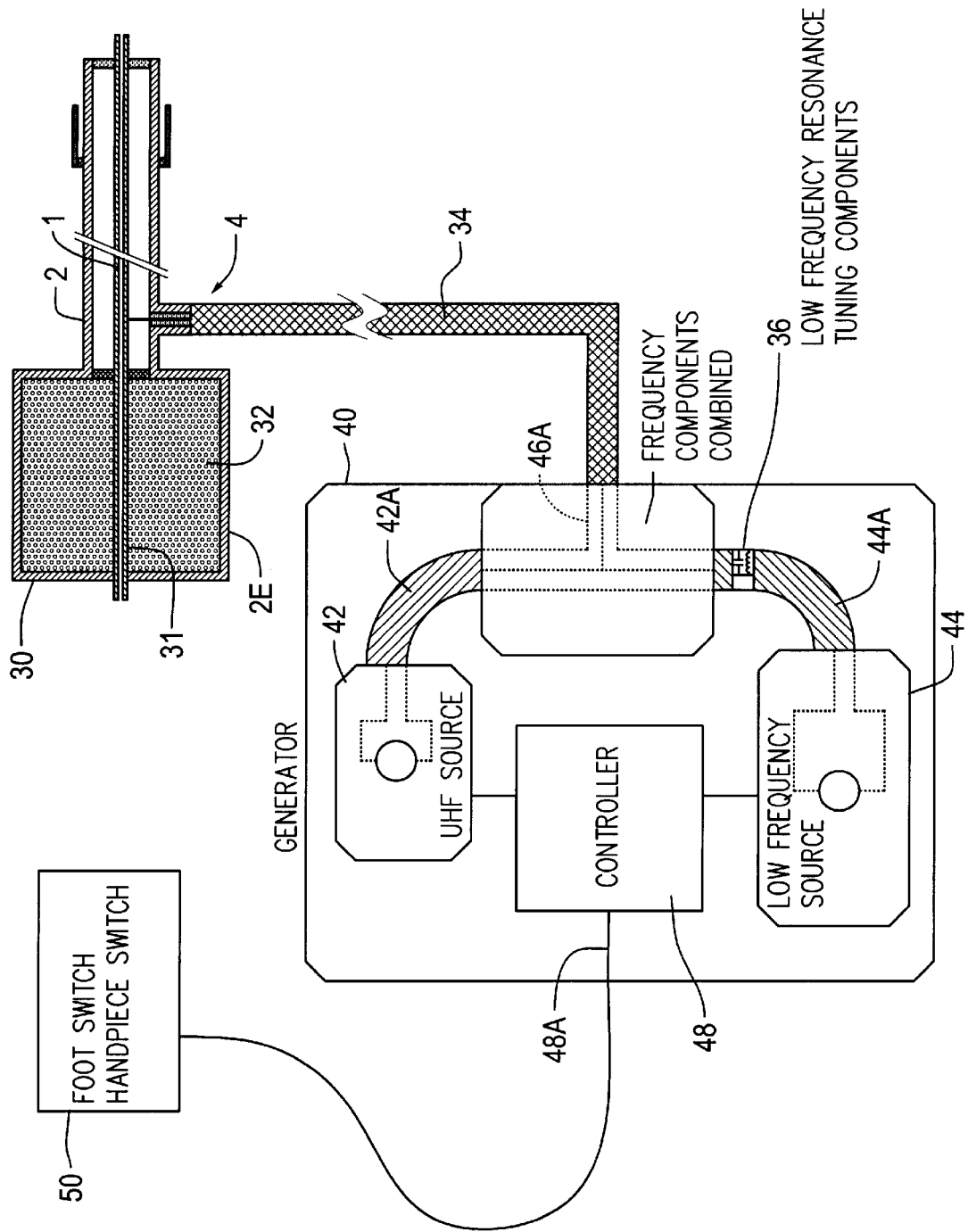
FIG. 5 is a diagram showing the tool converter of FIGS. 4A and 4B connected to an electrosurgical generator.

Referring to FIG. 5, which diagrammatically shows the instrument described above with reference to FIG. 4 connected to a dual frequency electrosurgical generator, the capacitance which resonates with the inductance 31, 32 at the lower operating frequency may be constituted by the feeder cable 34 itself and/or a lower frequency tuning reactance 36 (which may be capacitive or inductive, depending on the reactance of the cable 34) located in the feeder or, as shown in FIG. 5, in the generator 40.

The generator comprises two electrosurgical r.f. sources in the form of a first UHF source 32 operating at 2.45 GHz and a second, LF, source 44 operating typically at 5 MHz Each has a respective output line 42A, 44A feeding a combiner 46 which has an output 46A forming the output of the generator 40, which is connected to the feeder 4. The tuning reactance for low frequency isolation of the proximal end of the instrument here comprises a shunt reactance 36 in the line 44A. The two r.f. sources 42, 44 are controlled by a controller module 48 within the generator 40 which, in turn has an input 4A coupled to a foot switch or handpiece switch 50 for actuating the generator.

What is claimed is:
1. An electrosurgical instrument comprising:
   an elongate inner tubular member having a proximal end and a distal end, at least a portion of the inner member being electrically conductive in order that there is d.c. electrical continuity between said ends; and
   an elongate tubular electrically conductive sheath surrounding the inner member but spaced from the conductive material of the inner member to form an electrically insulative layer, whereby the inner member and the sheath constitute a coaxial transmission line, the sheath being electrically coupled to the inner member at a location spaced proximally from the distal end;
   a feeder coupled to the inner member distally of the connection between the sheath and the inner member; and
   an r.f. isolating structure between said couplings of the inner member to the feeder and to the sheath, the isolating structure presenting a series impedance between said couplings at an operating frequency of the instrument.

2. An instrument according to claim 1, wherein the isolating structure comprises a section of the inner member between said couplings, the section having an electrical length of $m\lambda/4$, where m is an odd number and $\lambda$ is the wavelength associated with the operating frequency.

3. An instrument according to claim 1, wherein the isolating structure includes an inductance formed by a section of the inner member between said couplings, the section being surrounded by a body of high permeability material.

4. An instrument according to claim 3, operable at upper and lower operating frequencies, wherein the isolating structure includes a further section of the inner member extending between the feeder and a decoupling capacitance, which capacitance is coupled between the inner member and the sheath at a location between the feeder and said inner member section surrounded by the high permeability body, the further inner member section having an electrical length of $m\lambda/4$, where m is an odd number and $\lambda$ is the wavelength associated with the upper operating frequency.

5. An instrument according to claim 1, wherein the isolating structure is resonant at an operating frequency of the instrument.

6. An instrument according to claim 3, further comprising a capacitor coupled between the sheath and a conductor of the feeder coupled to the inner member, the capacitor resonating with said inductance at an operating frequency of the instrument.

7. An instrument according to claim 1, wherein the insulative layer includes a dielectric optical material for transmitting illumination to the distal end of the inner member or for conveying imaging radiation from the distal end to the proximal end of the inner member.

8. An instrument according to claim 1, including a surgical tool having a metallic shaft housed inside said tubular inner member, the tool including a movable working element projecting from the distal end of the inner member and electronically coupled to the conductive member of the inner member.

9. An electrosurgical instrument for electrosurgical treatment at an operating frequency of at least 300 MHz, comprising an elongate electrically conductive lumen housing a mechanically or optically functional element, an electrode at a distal end of the lumen and electrically coupled to the lumen, an elongate electrically conductive outer sheath coaxially arranged around the lumen and having a distal end adjacent the lumen distal end, the sheath being dimensioned to enclose an electrically insulative layer such that the sheath and the lumen together form a coaxial transmission line, and an isolating structure associated with the distal end of the sheath to restrict the flow of electrosurgical currents in the sheath.

10. An instrument according to claim 9, wherein the isolating structure comprise a balun arranged to yield a substantially balanced feed location in the region of the distal end of the sheath.

11. An instrument according to claim 10, wherein the balun is a quarter-wave sleeve balun.

12. An instrument according to claim 9, wherein the sheath is proximally coupled to the lumen in respect of electrical currents at the operating frequency, and the lumen is coupled to a feed structure at a location spaced axially from said coupling to the sheath by a distance which is such that portions of the lumen extending proximally of the said coupling are electrically isolated from the feed structure at the operating frequency.

13. An instrument according to claim 12, wherein the feed structure includes a lateral aperture in the sheath.

14. An instrument according to claim 12, wherein the axial distance between the feed structure and the distal end of the sheath corresponds to an electrical length of substantially $n\lambda/2$, where n is an integer (1, 2, 3, . . . ) and $\lambda$ is the wavelength in said coaxial transmission line at the operating frequency.

15. An instrument according to claim 12, including a low frequency isolating choke associated with the lumen proximally of the feed structure, the choke being effective at a second operating frequency of less than 40 MHz.

16. An electrosurgical tool converter for converting an elongate surgical tool in an electrosurgical instrument for performing electrosurgical treatment at an operating frequency of at least 300 MHz, comprising an elongate electrically conductive lumen for receiving the tool with a working element of the tool exposed beyond an open distal end of the lumen to form an elongate electrically conductive outer sheath coaxially arranged around the lumen and having a distal end adjacent the lumen distal end, the sheath being dimensioned to enclose an electrically insulative layer such that the sheath and the lumen together form a coaxial transmission line, and an isolating structure associated with the distal end of the sheath to restrict the flow of electrosurgical currents in the sheath.

17. A tool converter according to claim 16, wherein the isolating structure comprises a balun arranged to yield a substantially balanced feed location in the region of the distal end of the sheath.

18. A tool converter according to claim 17, wherein the balun is a quarter-wave sleeve balun.

19. A tool converter according to claim 16, wherein the sheath is proximally coupled to the lumen in respect of electrical currents at the operating frequency, and the lumen is coupled to a feed structure at a location spaced axially from said coupling to the sheath by a distance which is such that portions of the lumen extending proximally of said coupling are electrically isolated from the feed structure at the operating frequency.

20. A tool converter according to claim 19, wherein the feed structure includes a lateral aperture in the sheath.

21. A tool converter according to claim 19, wherein the axial distance between the feed structure and the distal end of the sheath corresponds to an electrical length of substantially $n\lambda/2$, wherein n is an integer (1, 2, 3, . . . ) and $\lambda$ is the wavelength in said coaxial transmission line at the operating frequency.

22. A tool converter according to claim 19, including a low frequency isolating choke associated with tile lumen proximally of the feed structure, the choke being effective at a second operating frequency of less than 300 MHz.

23. A tool converter according to claim 22, where the choke is effective at an operating frequency of less than 40 MHz.

24. An electrosurgical instrument comprising the combination of a tool converter as claimed in claim 16, and a surgical tool housed in the lumen, the tool having a working clement projecting beyond the distal end of the lumen to form an electrode for electrosurgical treatment of tissue, and a handpiece projecting from a proximal end of the lumen.

25. A laparoscopic instrument according to claim 24.

26. An instrument according to claim 24, having a reciprocable actuation rod connected to a distal movable working element.

27. An instrument according to claim 26, constructed as forceps.

28. An instrument according to claim 26, constructed as scissors.

* * * * *